United States Patent
Imran

[11] Patent Number: 5,833,650
[45] Date of Patent: Nov. 10, 1998

[54] CATHETER APPARATUS AND METHOD FOR TREATING OCCLUDED VESSELS

[75] Inventor: Mir A. Imran, Palo Alto, Calif.

[73] Assignee: Percusurge, Inc., Sunnyvale, Calif.

[21] Appl. No.: 464,579

[22] Filed: Jun. 5, 1995

[51] Int. Cl.[6] .................................................. A61M 29/00
[52] U.S. Cl. ................................ 604/53; 604/49; 604/96; 604/101
[58] Field of Search ............................... 604/101, 96, 53; 606/194–196, 49

[56] References Cited

U.S. PATENT DOCUMENTS

| | | | |
|---|---|---|---|
| 4,445,892 | 5/1984 | Hussein et al. | 604/101 |
| 4,573,996 | 3/1986 | Weikl et al. | 604/53 |
| 4,771,777 | 9/1988 | Horzewski et al. | 128/344 |
| 4,832,028 | 5/1989 | Patel | 128/344 |
| 5,000,743 | 3/1991 | Patel | 606/194 |
| 5,135,484 | 8/1992 | Wright | 604/28 |
| 5,250,060 | 10/1993 | Carbo et al. | 606/159 |
| 5,281,200 | 1/1994 | Corso, Jr. et al. | 604/96 |
| 5,328,471 | 7/1994 | Slepian | 604/101 |
| 5,342,306 | 8/1994 | Don Michael | 604/101 |
| 5,380,284 | 1/1995 | Don Michael | 601/101 |
| 5,419,774 | 5/1995 | Willard et al. | 604/22 |

FOREIGN PATENT DOCUMENTS

WO 83/01894  6/1983  WIPO.

*Primary Examiner*—Wynnwood Coggins
*Assistant Examiner*—N. Kent Gring
*Attorney, Agent, or Firm*—Knobbe, Martens, Olson & Bear, L.L.P.

[57] ABSTRACT

A catheter assembly for treatment of a stenosis in a lumen in a blood-carrying vessel comprising a first flexible elongate tubular member having proximal and distal extremities. A first inflatable balloon is coaxially mounted on the distal extremity of the first flexible elongate tubular member and has a main lumen and an aspiration lumen exiting through the distal extremity. A second flexible elongate tubular member has proximal and distal extremities and has a second inflatable balloon coaxially mounted on the distal extremity and has a blood perfusion lumen extending therethrough. The second flexible elongate tubular member is slidably mounted in the main lumen of the first flexible elongate tubular member. The first balloon is positioned so that it is adjacent to but proximal of the stenosis and is thereafter inflated to create a first occlusion in the lumen in the vessel. A negative pressure is created in the lumen in the vessel distal of the first balloon through the aspiration lumen. The second balloon is positioned distal of the stenosis and is inflated to create a second occlusion in the lumen of the vessel to form a working space between the first and second balloons which brackets the stenosis. Blood is perfused through the blood perfusion lumen distal of the second occlusion. A therapeutic procedure is performed in the working space.

20 Claims, 10 Drawing Sheets

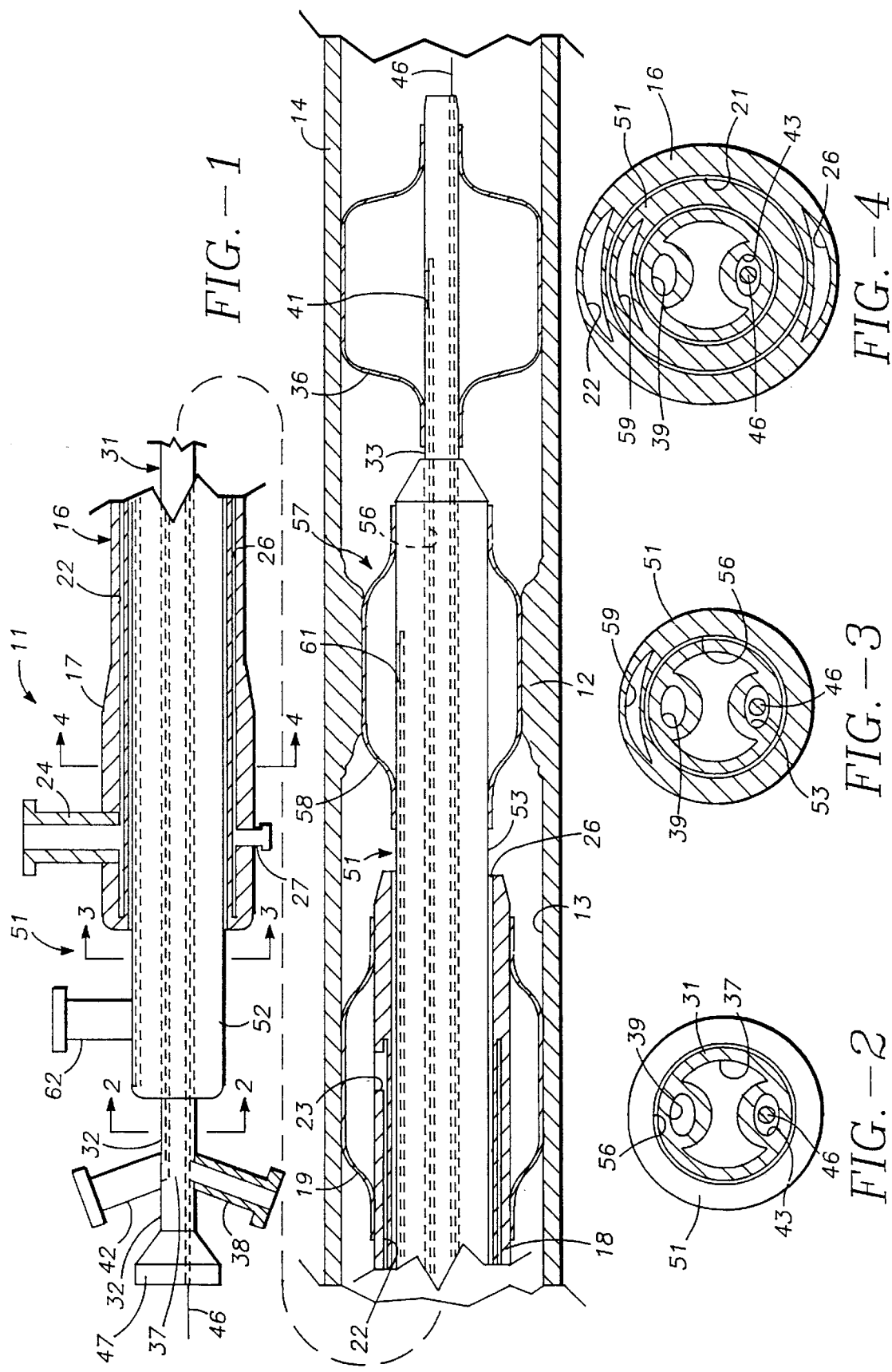

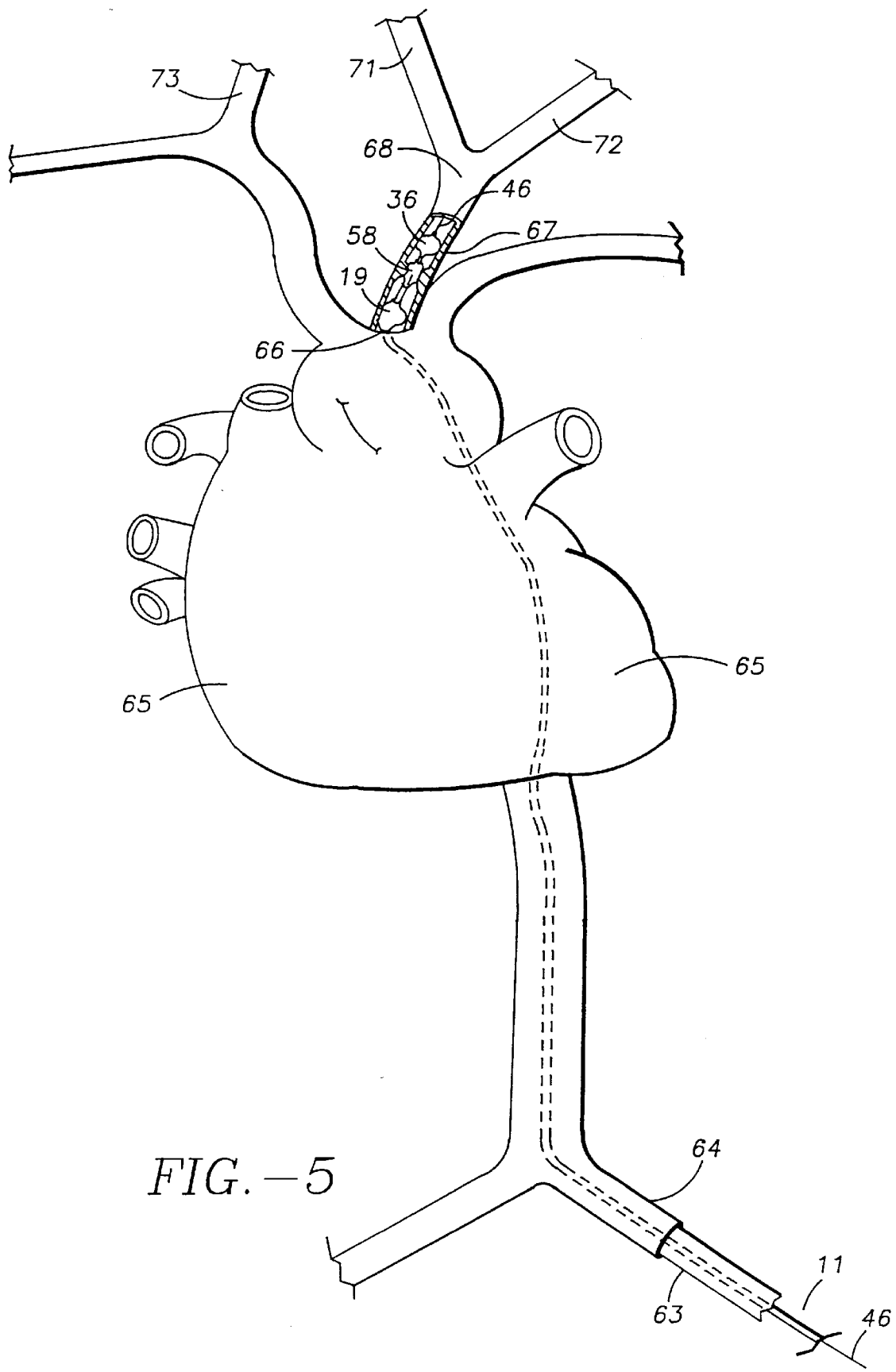

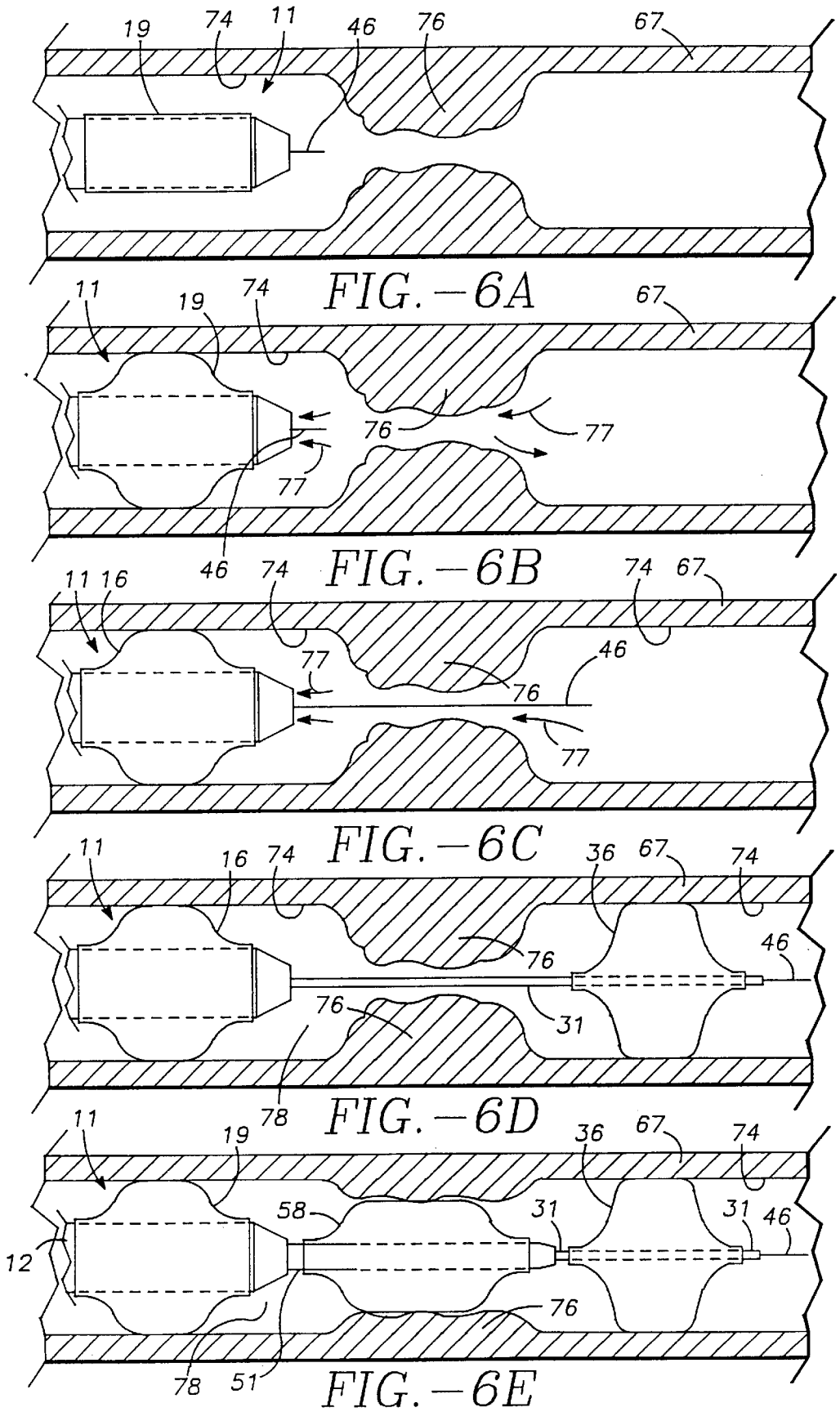

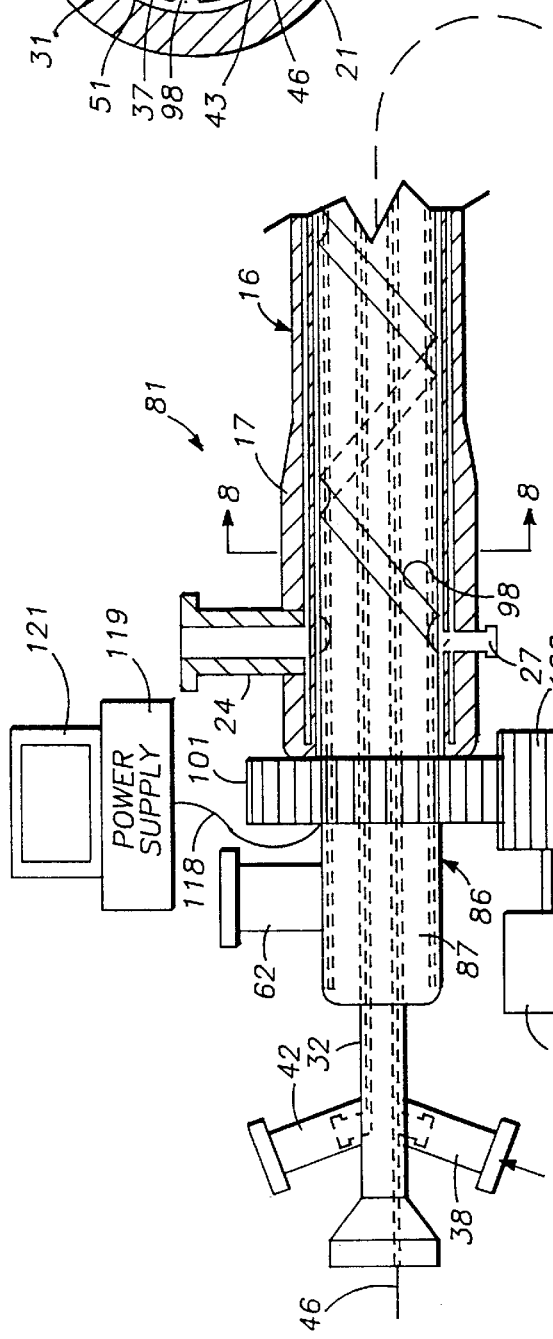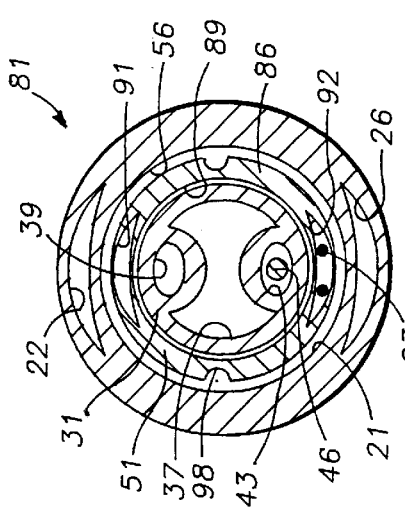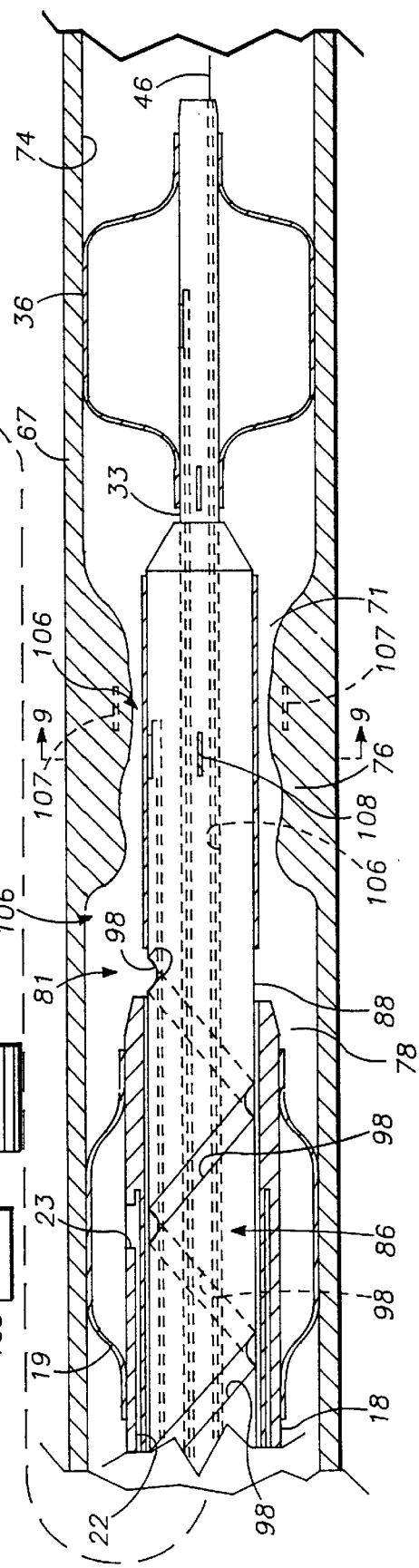

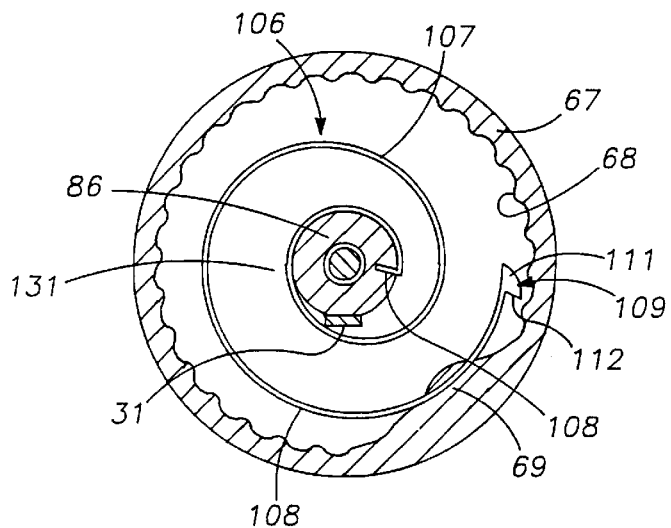
FIG.-9
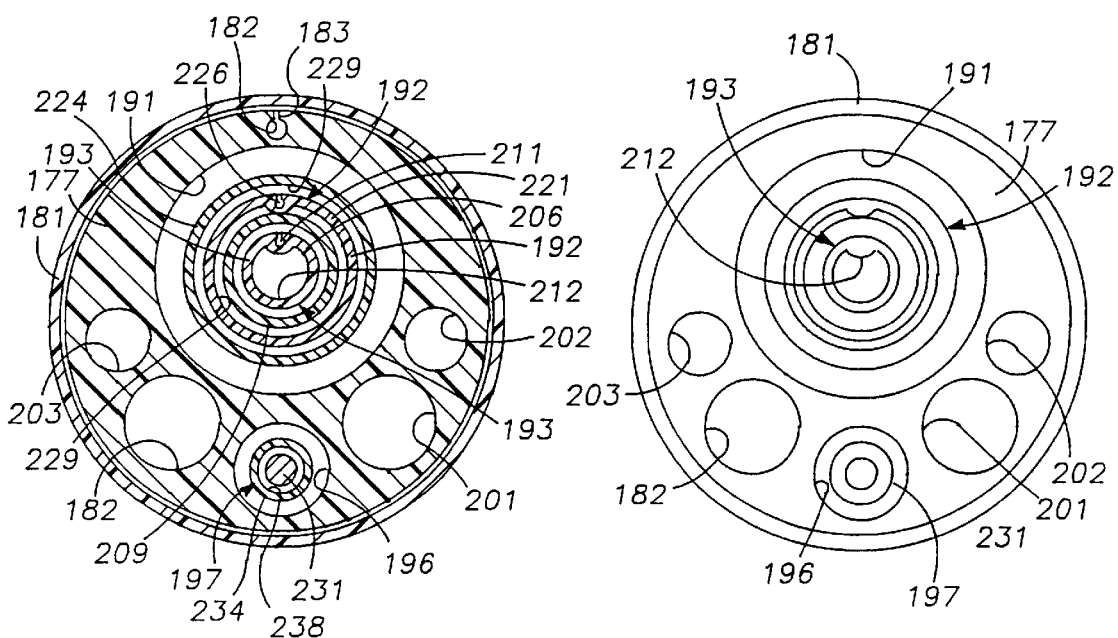
FIG.-13
FIG.-14

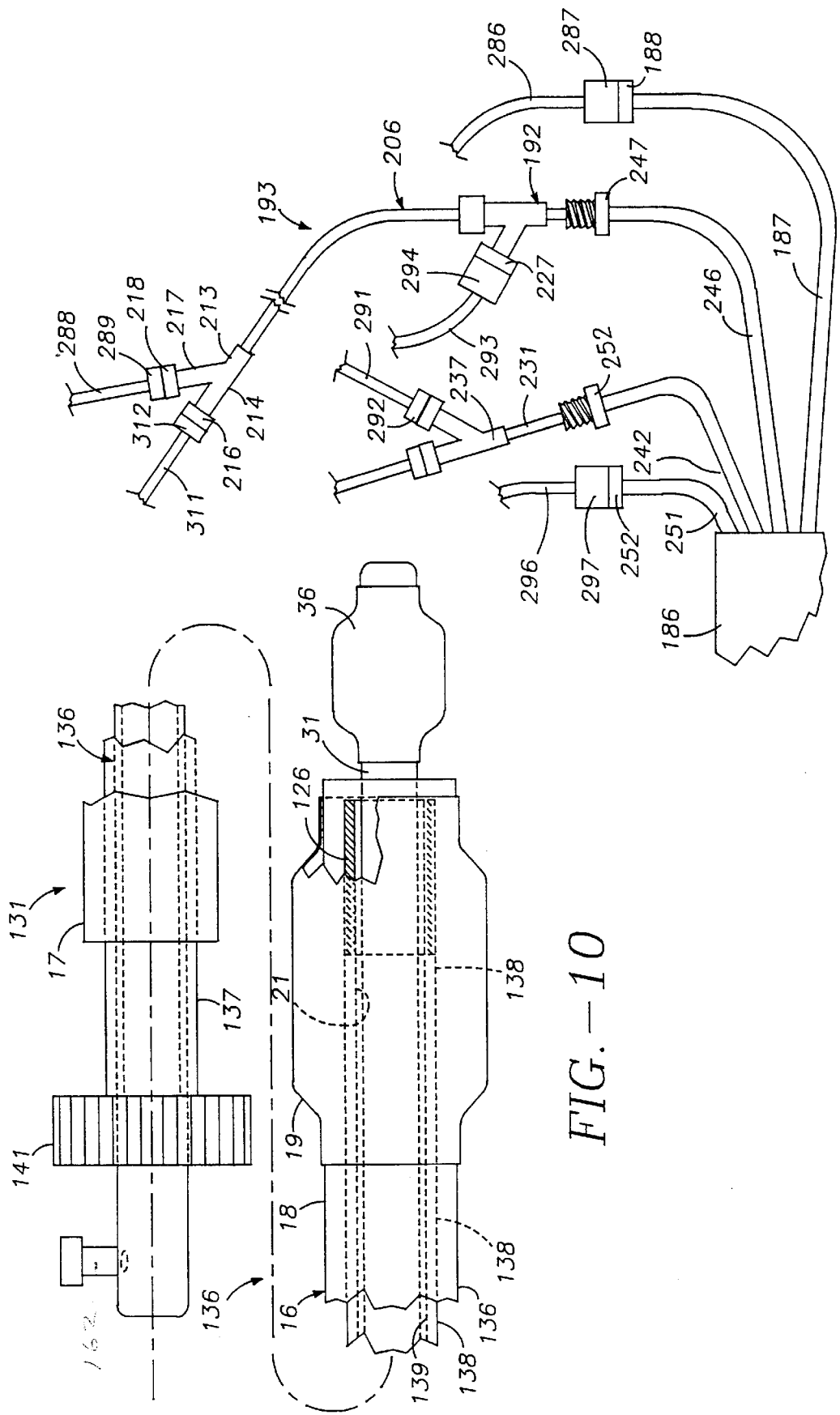

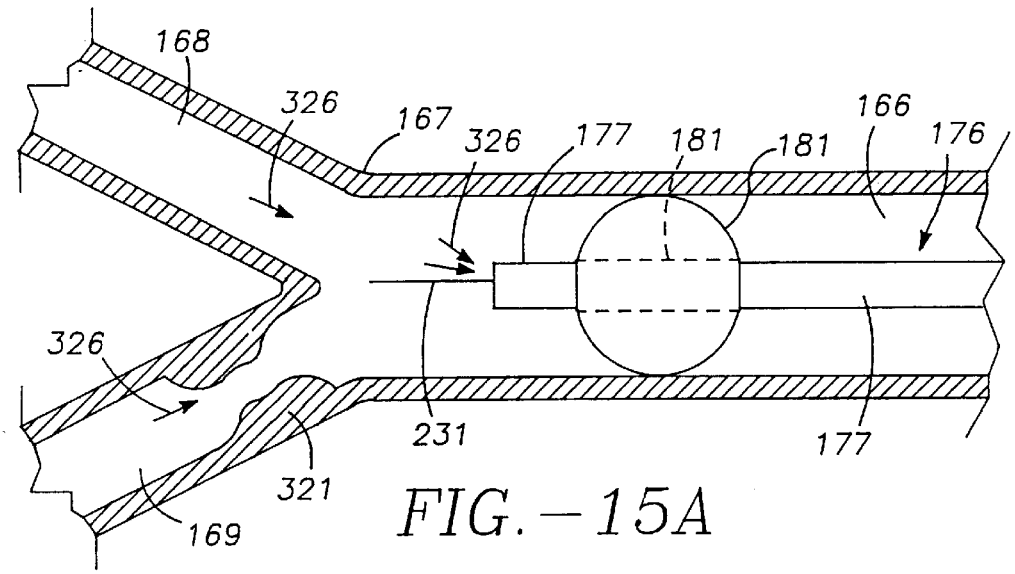
FIG.—15A
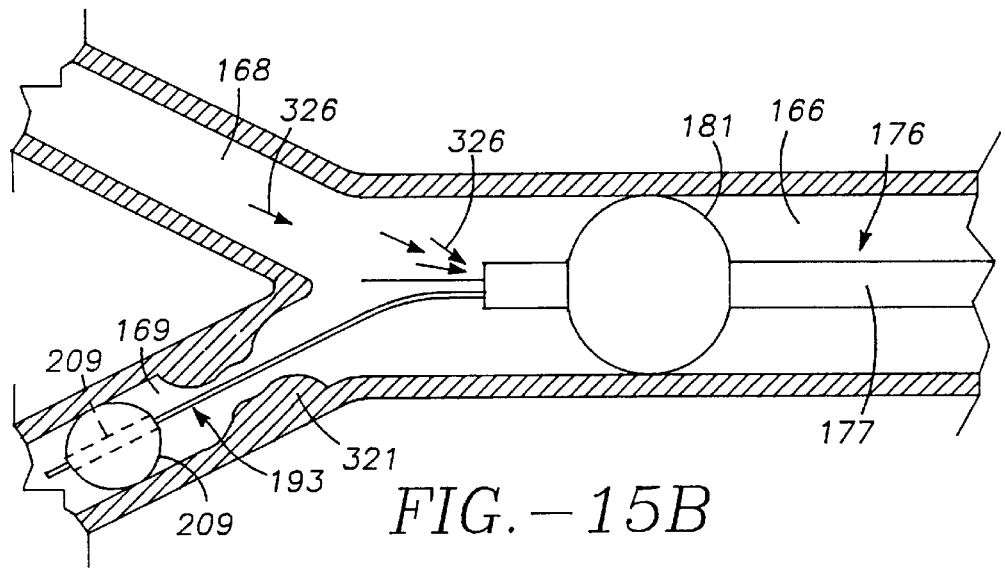
FIG.—15B
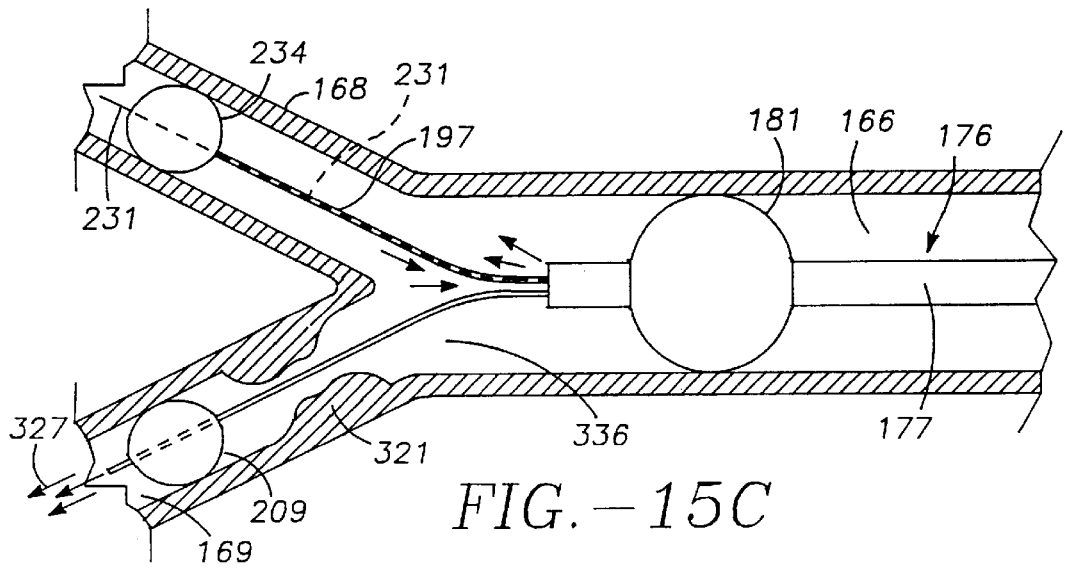
FIG.—15C

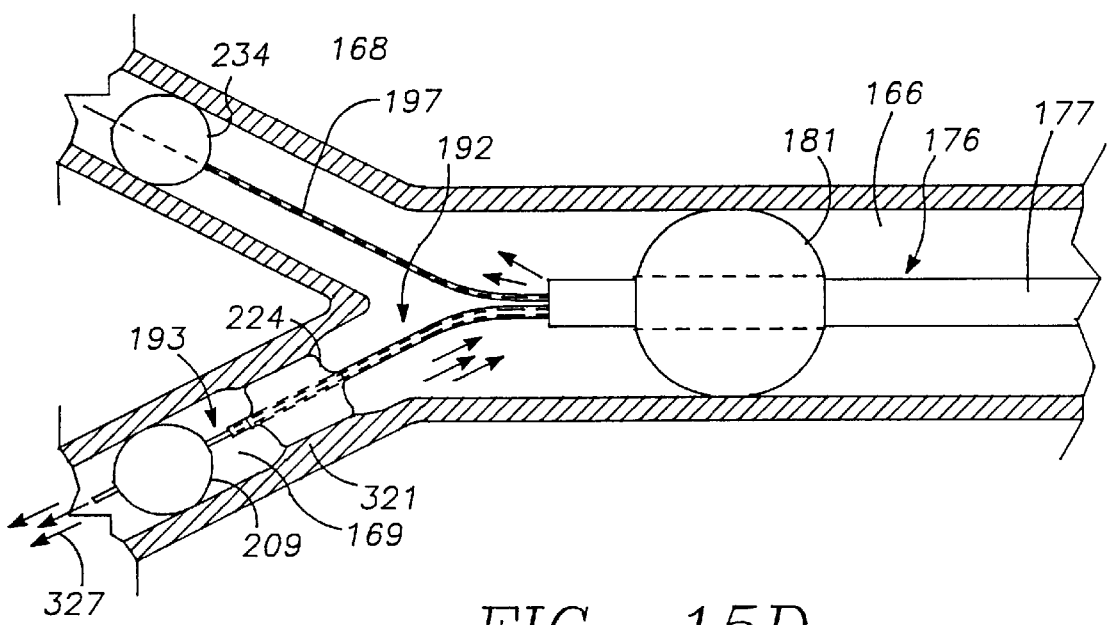
FIG.—15D

CATHETER APPARATUS AND METHOD FOR TREATING OCCLUDED VESSELS

This invention relates to an apparatus and method for treating occluded vessels in living bodies and more particularly for treating occlusions in carotid arteries.

Attempts heretofore have been made to treat occlusions in the carotid arteries leading to the brain. However, such arteries have been very difficult to treat because of the possibility of dislodging plaque which can enter various arterial vessels of the brain and cause permanent brain damage. Attempts to treat such occlusions with a balloon angioplasty have been very limited because of such dangers. In surgical treatments, the carotid artery has been slit and plaque removed from the slit area. Such surgical procedures have substantial risk associated with them which can lead to morbidity and mortality. In other procedures such as in angioplasty and in the treatment of peripheral arteries and veins, there is the possibility that the guide wires and catheters used in such procedures during deployment of the same may cause dislodgement of debris or emboli which can flow downstream and cause serious damage if they occlude blood flow in smaller vessels. There is therefore need for new and improved apparatus and methods which makes it possible to treat occluded vessels without endangering the patient.

In general, it is an object of the present invention to provide a catheter apparatus or assembly and method for treating occluded vessels which makes it possible to prevent downstream flow of debris or emboli.

Another object of the invention is to provide an apparatus and method which makes it possible to reverse the flow of blood in an occluded vessel during the time that a stenosis is being crossed.

Another object of the invention is to provide an apparatus and method of the above character in which a negative pressure is created within the vessel to reverse the flow of blood in the vessel.

Another object of the invention is to provide an apparatus and method of the above character in which it is only necessary to stop the flow of blood in a vessel of a patient for a very short period of time.

Another object of the invention is to provide an apparatus and method in which a working space is provided in the vessel free of blood for treatment of the stenosis.

Another object of the invention is to provide an apparatus and method of the above character in which material which is removed during the treatment of the occlusion or stenosis is removed by suction.

Another object of the invention is to provide an apparatus and method of the above character in which blood is shunted around the working space.

Another object of the invention is to provide an apparatus and method in which a cutting device is utilized for treatment of the stenosis or atheroma in the vessel and in which the material removed from the stenosis or atheroma is aspirated out of the operating space.

Another object of the invention is to provide an apparatus and method of the above character in which the amount of material removed from the stenosis or atheroma can be precisely controlled.

Another object of the invention is to provide an apparatus and method of the above character which makes it possible to treat stenoses or occlusion in the vessel which are normally not accessible for surgical procedures.

Another object of the invention is to provide an apparatus and method of the above character which utilizes two spaced apart balloons to create the working space in the vessel.

Another object of the invention is to provide an apparatus and method of the above character that can be utilized to create a working space in a vessel having a bifurcation therein and in which the working space includes the bifurcation.

Another object of the invention is to provide an apparatus and method of the above character which utilizes three spaced apart balloons to create the working space in the vessel having a bifurcation therein.

Another object of the invention is to provide an apparatus and method of the above character which includes a control console for controlling the inflation of the blood flow pump.

Another object of the invention is to provide an apparatus and method of the above character which is particularly adapted for use with the carotid vessels.

Additional objects and features of the invention will appear from the following description in which the preferred embodiments are set forth in detail in conjunction with the accompanying drawings.

FIG. 1 is a side elevational view partially in section showing the catheter apparatus or assembly of the present invention for treating occluded vessels.

FIG. 2 is a cross-sectional view taken along the line 2—2 of FIG. 1.

FIG. 3 is a cross-sectional view taken along the line 3—3 of FIG. 1.

FIG. 4 is a cross-sectional view taken along the line 4—4 of FIG. 1.

FIG. 5 is a schematic illustration of how the catheter apparatus shown in FIG. 1 is deployed in a carotid artery.

FIGS. 6A—6E are illustrations showing the various steps utilized in deployment of the catheter apparatus in performing the method of the present invention in a vessel where a bifurcation is not present.

FIG. 7 is a side elevational view partially in section of another embodiment of a catheter apparatus or assembly incorporating the present invention for treating occluded vessels using an atherectomy device.

FIG. 8 is a cross-sectional view taken along the line 8—8 of FIG. 7.

FIG. 9 is a cross-sectional view taken along the line 9—9 of FIG. 7.

FIG. 10 is a side elevational view in section of the distal extremity of another embodiment of a catheter apparatus incorporating the present invention and utilized for delivering an expandable stent to a stenosis.

Figure 11A:
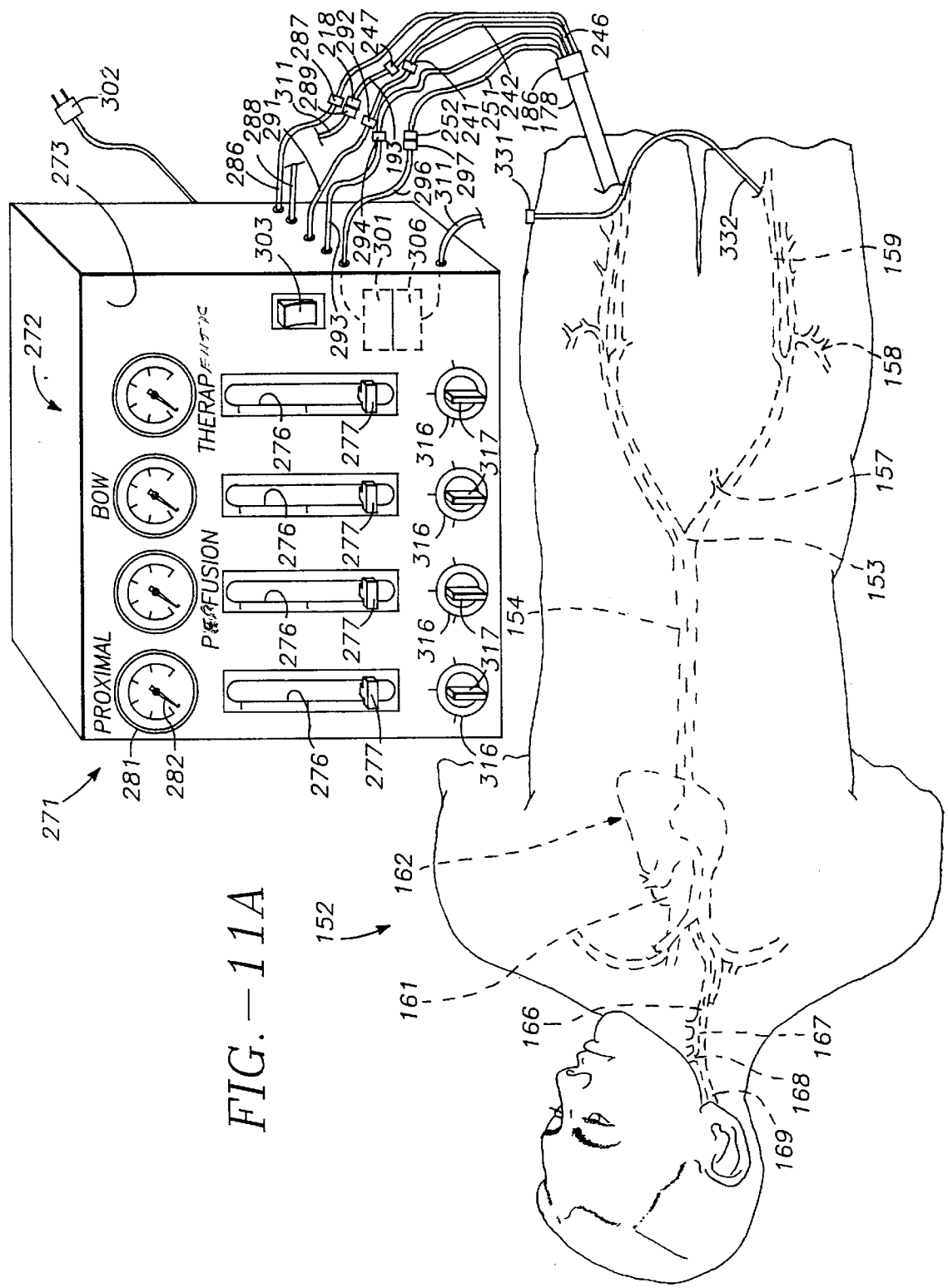

FIG. 11A is a schematic illustration showing the manner in which the apparatus of the present invention is utilized in connection with vessels of a patient in performing the method of the present invention.

FIG. 11B is an additional partial schematic illustration showing interconnections in the catheter apparatus shown in FIG. 11A.

Figure 12:
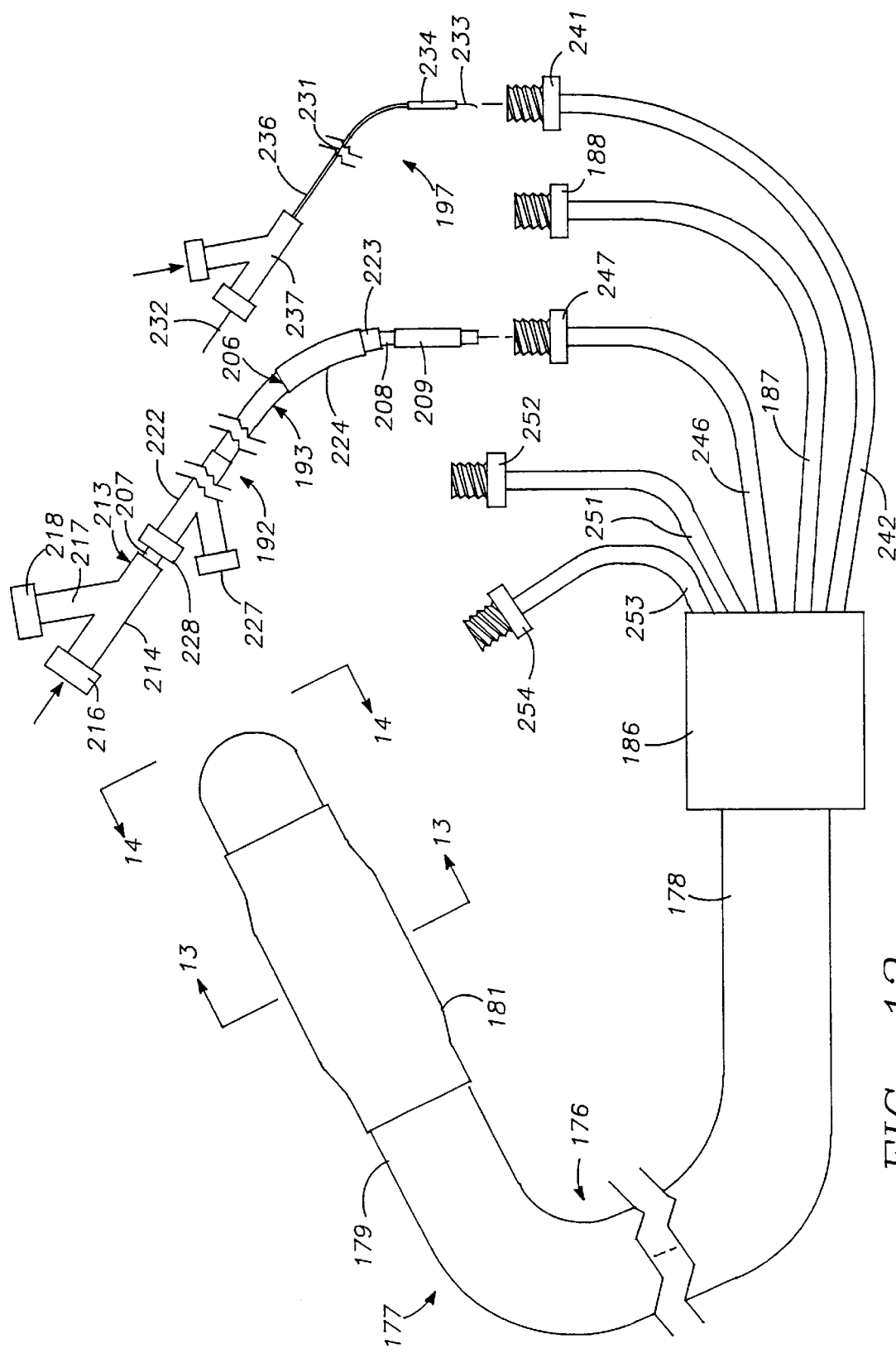

FIG. 12 is a plan view of another embodiment of a catheter apparatus incorporating the present invention.

FIG. 13 is a cross-sectional view taken along the line 13—13 of FIG. 12.

FIG. 14 is an enlarged isometric view of the control console shown in FIG. 11 utilized in the present invention.

FIGS. 15A, B, C, D and E are illustrations showing the method of the present invention being utilized with the apparatus shown in FIG. 11 in a vessel having a bifurcation therein.

In general, the catheter apparatus of the present invention is for treatment of a stenosis in a lumen in a blood carrying vessel in which the stenosis has a length and a width or thickness which at least partially occludes the lumen in the vessel. The apparatus is comprised of a first flexible elongate tubular member having proximal and distal extremities. A first inflatable elastic balloon is coaxially mounted on the distal extremity of the first tubular member. The first tubular member has therein a centrally disposed lumen, a balloon inflation lumen in communication with the interior of the first inflatable balloon and an aspiration lumen exiting through the distal extremity. A second flexible elongate tubular member is provided which extends through the centrally disposed lumen of the first tubular member and has proximal and distal extremities. A second inflatable balloon is coaxially mounted on the distal extremity of the second tubular member. The second tubular member has a balloon inflation lumen therein in communication with the interior of the second balloon. The second tubular member is also provided with a guide wire and/or fluid flow lumen for or blood. Means is carried by the proximal extremity of the first and second tubular members permitting advancement of the first balloon into position proximal of the occlusion in the vessel and for inflating the same and for creating suction on the aspiration lumen to aspirate the space in the vessel distal of the first balloon and thereafter permitting placement of the second balloon distal of the occlusion and inflation of the second balloon to create a working space between the first and second balloons and for shunting arterial blood from the arterial blood flow lumen into the vessel distal of the second balloon. A third flexible elongate tubular member is provided which extends through the centrally disposed lumen of the first tubular member and has a lumen therein through which the second tubular member extends. Means is carried by the distal extremity of the third tubular member for performing a medical procedure in the working space created between the first and second balloons which brackets the stenosis.

More particularly as shown in FIGS. 1–4 of the drawings, the catheter apparatus 11 of the present invention which is for use in the treatment of a stenosis 12 in a lumen 13 in a blood-carrying vessel 14 in which the stenosis 12 has a length and a width or thickness which at least partially occludes the lumen 13. The apparatus consists of a first elongate flexible tubular member 16 formed of a suitable plastic material which is provided with proximal and distal extremities 17 and 18. A first balloon 19 is mounted on the distal extremity 18 and preferably is a compliant balloon formed of a suitable elastic material such as a latex or a very low radiation polyethylene so that it can be inflated to the size of the vessel 12 in which it is to be disposed. Thus, the balloon 19 should be capable of expanding to various diameters depending on the size of the vessel. The first balloon 19 can be formed as a separate balloon separate from the elongate tubular member 16 as shown and adhered thereto by suitable means such as an adhesive (not shown), or it can be formed integral with the tubular member 16 in a manner well known to those skilled in the art.

The tubular member 16 is provided with a large centrally disposed or main lumen 21 extending from the proximal extremity 17 to the distal extremity 18. It is also provided with a balloon inflation lumen 22 which has a distal extremity in communication with the interior of the first balloon 16 through a port 23. The proximal extremity of the balloon inflation lumen 22 is in communication with a balloon inflation fitting 24 mounted on the proximal extremity 13 of the tubular member 12. The fitting 24 can be of a conventional type as for example a Luer-type fitting which is adapted to be connected to a balloon inflation device (not shown) for inflating and deflating the first balloon 16.

The first tubular member 16 is also provided with an aspiration lumen 26 which exits through the distal extremity 13 and the proximal extremity 14 of the tubular member 12. A Luer-type fitting 27 is mounted on the proximal extremity 14 and is in communication with the aspiration lumen 26. The fitting 27 is adapted to be connected to a suitable aspiration or suction source (not shown) of a conventional type for aspiration purposes as hereinafter described.

The catheter assembly or apparatus 11 also consists of a second elongate flexible tubular member 31 having proximal and distal extremities 32 and 33. A second inflatable balloon 36 of the same type as the first inflatable balloon is coaxially mounted on the distal extremity 33 in a conventional manner. The tubular member 31 is provided with a large generally centrally disposed arterial blood flow lumen 37 which opens through the distal extremity 33 and is in communication with a Luer-type fitting 38 which as hereinafter described is adapted to be connected to a supply of arterial blood from the patient which for example can be taken from another femoral artery of the patient by the use of a blood pump.

The second tubular member 31 is also provided with a balloon inflation lumen 39 which is in communication with the interior of the second inflatable balloon 36 through a port 41. The proximal extremity of the lumen 39 is in communication with the Luer-type fitting 42 mounted on the proximal extremity 32 of the second tubular member 31 and as with the balloon inflation fitting 24 is adapted to be connected to a balloon inflation deflation device (not shown) of a conventional type. The second tubular member 31 is also provided with a lumen 43 which also can be used as a guide wire and/or for introducing a saline solution extending from the proximal extremity to the distal extremity. The lumen 43 is sized so that it is adapted to receive a conventional guide wire 46 as for example a 0.014" or 0.018" guide wire and extends from the proximal extremity to the distal extremity so that the guide wire 46 can extend beyond the distal extremity of the second tubular member 31. A fitting 47 is provided on the proximal extremity 32 in communication with the lumen 43 for introducing the saline solution.

As shown in FIG. 1, the second tubular member 31 is disposed within the central lumen 21 of the first tubular member 12 and is slidably and coaxially mounted therein for displacement of the second balloon 36 with respect to the first balloon 16 as hereinafter described.

The catheter assembly or apparatus 11 also consists of a third elongate flexible tubular member 51 having proximal and distal extremities 52 and 53. It is provided with a centrally disposed lumen 56 extending from the proximal extremity 52 to the distal extremity 53 and through which the second tubular member 31 is coaxially and slidably mounted.

Means 57 is provided on the distal extremity 53 of the third tubular member 51 for performing a medical procedure. In the embodiment of the invention shown in FIG. 1, this means 57 consists of a third balloon 58 which can be non-compliant coaxially mounted on the distal extremity of the third tubular member 51. The third balloon 58 can be attached in the same manner as the first and second balloons 19 and 36 hereinbefore described. The third tubular member 51 is provided with a balloon inflation lumen 59 which has its distal extremity in communication with the interior of the balloon 58 through a port 61. The proximal extremity of the balloon inflation 59 is in communication with a Luer-type fitting 62 provided on the proximal extremity 52 and adapted to be connected to a conventional inflation deflation device (not shown) for inflating and deflating the third balloon 58.

The operation and use of the catheter assembly or apparatus 11 in the method of the present invention for treating occluded vessels may now be briefly described in connection with an occlusion formed by a stenosis in a vessel not having a bifurcation therein as for example in saphenous graft or in one of the right and left carotid arteries, also called internal and external carotid arteries, of a patient in connection with the illustrations shown in FIGS. 5 and 6A–6E. A guiding catheter 63 (FIG. 5) of a conventional type is inserted into an incision into a femoral artery of a patient and is advanced through that artery into the aorta 64 of the heart 65 of the patient and into the ostium 66 of the selected carotid artery or vessel as for example the left carotid 67. As is well known to those skilled in the art of anatomy, the left carotid 67 is provided with a bifurcation 68 which leads to internal and external carotids 71 and 72. A right carotid 73 is provided which also extends into a bifurcation (not shown) and internal and external carotids (not shown).

After the guiding catheter has been appropriately positioned, the guide wire 46 is introduced separately into the guiding catheter or along with the catheter assembly 11. The distal extremity of the catheter apparatus or assembly 11 with all of the first, second and third balloons 19, 36 and 58 completely deflated, is introduced into the guiding catheter 63 along with or over the guide wire 46 and is advanced through the guiding catheter 63 into the ostium 66 of the carotid artery or vessel 67 and into the lumen or passageway 68 of the vessel as shown in FIGS. 5 and 6B.

The distal extremity of the catheter assembly 11 is advanced until it is just proximal of a stenosis 76 in the carotid artery 67 to be treated. The balloon 19 is then inflated by introducing a suitable inflation medium such as a radiopaque liquid into the fitting 24 to cause it to pass through the balloon inflation lumen 22 through the port 23 and into the interior of the first balloon 19 to inflate the same as shown in FIG. 6A. The balloon 19 is progressively inflated until it engages the side wall of the vessel 67 to occlude the vessel 67. At the time that this is occurring, a negative pressure or suction is applied to the aspiration fitting 27 to supply a negative pressure through the balloon inflation lumen 22 to suck or aspirate blood in the vessel 67 distal of the first balloon 16 into the lumen and out the aspiration port 62 to thereby reverse the flow of blood through the stenosis as shown by the arrows 71 in FIG. 6B.

While a reverse flow of blood is occurring in the vessel 67, the guide wire 46 is advanced through the stenosis 76 as shown in FIG. 6C. In the event that any pieces or particles of plaque are knocked off of the occlusion formed by the stenosis 76 by movement of the guide wire 46 through the same, such pieces of plaque or emboli will be drawn out with the reverse flow of blood into the aspiration lumen 26 and out of the aspiration fitting 27. During the time that the guide wire 46 is being advanced through the stenosis 67 it may be desirable at the same time to introduce a saline solution through the guide wire lumen 43 of the second elongate flexible tubular member 31 to exit through the distal extremity of the second elongate flexible tubular member 31 into the space immediately proximal of the stenosis 67. This introduced saline solution aids the flow of particulate or other particles dislodged from the stenosis 76 during advancement of the guide wire 46 through the same and carries them back with the mixed saline blood solution through the aspiration lumen 26 in a manner hereinbefore described.

With the guide wire 46 remaining in position, the second elongate flexible tubular member 31 with the second balloon 36 thereon in a deflated condition is advanced over the guide wire 46 through the stenosis 76 until -the second balloon 36 is distal of the stenosis 76 as shown in FIG. 6D after which the second balloon 36 is inflated by introducing an inflation medium as for example a radiopaque liquid through the inflation fitting 42 into the lumen 39 through the port 41 to the interior of the second balloon 36 to inflate the second balloon 36 until it engages the sidewall of the vessel 67.

Prior to, during or after inflation of the second balloon 36, the guide wire 46 can be removed. However, it is preferable to remove the guide wire 46 as soon as the second balloon 36 has been advanced so that it is beyond the stenosis 76. At this time, and certainly prior to complete inflation of the second balloon 36, blood is shunted across the stenosis 76 and into the lumen 68 distal of the second balloon 36 by introducing blood through the fitting 38 and into the centrally disposed blood flow lumen 37 in the second tubular member 31 so that it exits out the central lumen 37 distal of the second balloon 36. The blood which is supplied to the fitting 37 can be taken from another femoral artery of the patient and pumped into the fitting 38. In addition, if desired, the blood which is aspirated in the space distal of the first balloon 16 can be appropriately filtered and also supplied to the fitting 38. By shunting blood past the stenosis 69 in this manner it can be seen that blood is being continuously supplied to the carotid artery of the patient during the time that the second balloon 36 is inflated and occludes the lumen 68 in the vessel 67.

As soon as the second balloon 36 has been inflated, it can be seen that there is provided a working space 78 (FIG. 6D) between the first and second balloons 19 and 36 so that medical procedures can be undertaken to remove or reduce the stenosis 76 in the space between the first and second balloons 19 and 36.

Assuming that it is desired to compress the plaque or material forming the stenosis 76 to provide a larger lumen, -opening or passageway through the stenosis 76, the third tubular member 51 can be advanced by grasping the proximal extremity 52 to cause the distal extremity with the third balloon 58 thereon to be advanced into the space 78. As soon as the balloon 58 has been properly positioned within the stenosis 76, the balloon 58 also can be inflated with a suitable inflation medium as for example a radiopaque liquid. The balloon 58 can be inflated to the desired pressure to cause compression of the plaque of the occlusion against the sidewall of the vessel 67 by the application of appropriate pressure. As in conventional angioplasty procedures, the third balloon 58 can be formed of a non-elastic relatively non-compliant material so that high pressures as for example 10–15 atmospheres can be used within the balloon to apply compressive forces to the vessel without danger of rupturing the vessel. It should be appreciated that the non-elastic capabilities can also be achieved by a composite elastic material.

Since the blood flow has been restored to the vessel 67 by the shunt hereinbefore described, the compression of the occlusion forming the stenosis 76 can be carried out for an extended period of time, as for example after a few minutes, if desired to help ensure that a large lumen or passageway is formed through the stenosis 76 as shown in FIG. 6E. If it is believed that the occlusion forming the stenosis 69 has been sufficiently compressed, the third balloon 58 can be deflated. In the event an inelastic balloon is utilized for the third balloon 58, and it is desired to utilize a larger third balloon, this can be accomplished by removing the third tubular member 51 with the deflated balloon 58 thereon and introducing a third tubular member 51 having a larger size balloon thereon over the second tubular member 31 and advancing it into the stenosis 69 and inflating the larger size balloon to create a still larger passage through the stenosis 76.

After the appropriate dilation the stenosis 76 has been accomplished the third balloon can be removed from the stenosis while aspiration of the space 78 is still ongoing so that any plaque coming off the occlusion forming the stenosis 67 can be aspirated out of the vessel. After the third balloon 58 has been removed from the stenosis, the second balloon 36 and the first balloon 16 can be deflated to permit normal blood flow through the vessel 61 after which the arterial blood flow supply to the fitting 38 can be terminated. The entire catheter assembly 11 can then be removed from the guiding catheter 63 after which the guiding catheter 63 can be removed and a suture applied to the incision created to obtain access to the femoral artery.

In place of the third balloon 58 for causing compression of the occlusion forming the stenosis 67 to create a larger passageway therethrough, an atherectomy device 81 can be utilized for operating in the working space 78 to remove the plaque of the occlusion forming the stenosis. This can be accomplished with a catheter assembly or apparatus 81 which in many respects is similar to the apparatus 11 shown in FIG. 1 and consists of a first tubular member 16 with a first balloon 19 and a second tubular 31 with a second balloon 36 thereon. In place of the third flexible elongate tubular member 51 there is provided a third flexible elongate tubular member 86 which is provided with proximal and distal extremities 87 and 88. The flexible elongate tubular member 86 is slidably and rotatably mounted in the central lumen 21 of the flexible elongate member 16 and is provided with a central or main lumen 89 through which the second flexible elongate tubular member 31 extends. It is also provided with a lumen 91 extending from the proximal extremity to the distal extremity through which a saline solution can be introduced for saline irrigation as hereinafter described. It is also provided with another lumen 92 which is adapted to receive a plurality of electrical conductors 93 for performing electrical functions as hereinafter described. The lumen 92 is connected to a conventional Luer-type fitting 96 serving as a fluid irrigation fitting mounted on the proximal extremity first tubular member 12 and is in communication with an annular recess 97 which is in communication with the lumen 91 provided in the tubular member 86 for supplying a saline irrigation liquid through the flexible elongate tubular member 86 and into the working space 78 provided between the first and second balloons 16 and 36. In order to aid aspiration of the saline irrigation liquid from the working space 78, the outer surface of the flexible elongate tubular member 86 is provided with a helical groove 98 therein which has one end which opens into the working space 78 and which has the other end in communication with the aspiration fitting 27.

Means is provided for rotating the second tubular member 86 and consists of suitable means such as a spur gear 101 mounted on the proximal extremity 87 of the tubular member 86. The spur gear 101 is driven in a suitable manner as for example by another smaller spur gear 102 which is of greater width than spur gear 101 so as to provide a splined gear connection between the gears 101 and 102. This accommodates the desired longitudinal movement for the tubular member 86 so that the distal extremity 88 of the tubular member 86 can be advanced and retracted in the working space 78 as hereinbefore described. An electrical drive motor 103 is provided for driving the gear 102.

Atherectomy means 106 is provided on the distal extremity 88 of the flexible elongate tubular member 86. As shown in FIGS. 7 and 9, the atherectomy means 106 consists of a flexible elongate member 107 formed of a suitable material such as stainless steel or preferably a superelastic Nitinol. The flexible elongate member 107 is wound into a helix as shown in FIG. 9 onto the distal extremity of the tubular member 86. The flexible elongate member 107 can be formed of a ribbon having a thickness of 0.003" and a width of 0.060". One end of the flexible elongate member 107 can be secured to the tubular member 86, as for example by inserting the same into a slit 108 and additionally by the use of adhesive (not shown). The flexible elongate member 107 is wrapped into a helix in a direction opposite to the direction of normal rotation of the tubular member 86 and can be provided with a special tip 109 on its free end with the tip having an arcuate surface 111 that is inclined rearwardly to terminate at a cutting edge 112 (see FIG. 9) which is adapted to engage the plaque or the stenosis 76.

When the distal extremity 88 of the flexible elongate tubular member 86 has been introduced into the working space 78, the end or tip 109 of the flexible elongate member 107 of the atherectomy means 106 is free. A saline solution is introduced into the fitting 57. Thereafter the motor 103 can be energized to cause rotation of the tubular member 86 and to thereby cause rotation of the helically wound flexible elongate member 107 to cause its free end or tip 109 to be moved outwardly radially under centrifugal force to bring the cutting edge 112 into engagement with the plaque 69 in the stenosis 76 to cause progressive removal of the plaque forming the stenosis 76 to enlarge the passageway extending through the stenosis. Because of the rounded configuration of the tip 109, the tip 109 will not dig into the vessel wall but will only remove plaque which is engaged by the cutting edge 112. As the plaque is being removed, the saline solution introduced through the fitting 96 into the space 78 picks up the plaque particles or emboli as they are being removed. The saline solution with the plaque or emboli therein is removed through the spiral groove 98 and through the aspiration port 27. The flexible elongate tubular member 86 can be moved back and forth so that the cutting tip 109 engages the length of the stenosis 76 so that substantially all of the stenosis 76 can be removed.

Means is provided to sense when sufficient plaque has been removed from the stenosis 76 and to ensure that cutting edge 112 does not cut into the vessel wall. An ultrasonic sensor 116 is mounted in the distal extremity of the tubular member 86 and is connected by conductors 93 extending through the lumen 92 and connected to a cable 118 which is connected to an ultrasonic power supply 119 and a video monitor 121. By using the Doppler effect, ultrasonic energy can be utilized in connection with the transducer 116 to ascertain the depth of cut being made by the flexible elongate member 107 as it is being rotated.

As soon as a desired amount of plaque has been removed from the stenosis 69 to provide the desired passage through the stenosis, rotation of the tubular member 86 is terminated after which the tubular member 86 can be withdrawn followed by deflation of the second balloon 36 and withdrawing it, deflation of the first balloon 16 and withdrawing it from the vessel 67. Thereafter, the guiding catheter 63 can be removed and the incision closed as hereinbefore described.

In order to ensure that restenosis will not take place, it may be desirable to place a cylindrical stent 126 in the stenosis 76. Such a stent 126 can be a self-expanding stent formed of a suitable material such as a superelastic Nitinol and movable between unexpanded and expanded conditions. Such a stent 126 can be placed by a suitable catheter apparatus 131 of the type shown in FIG. 10. The stent 126 which is cylindrical in form is pushed over the proximal extremity of the second elongate flexible tubular member 31 into the main or central lumen 21 so that it is retained in the unexpanded position. It is then pushed forwardly toward the distal extremity of the first flexible elongate tubular member 16 by means of a flexible elongate tubular member 136 having proximal and distal extremities 137 and 138 and having a flow passage 139 extending from the proximal extremity 137 to the distal extremity 138. The proximal extremity 137 is provided with a knurled collar 141 which is adapted to be engaged by the hand to facilitate pushing of the flexible elongate tubular member 136 so that its distal extremity is in engagement with the stent 126. Thus, when desired the stent 126 may be discharged or dislodged from the distal extremity of the second tubular member 31 and pushed into the working space 71 created between the first balloon 19 and the second balloon 36.

After the stent 126 has been discharged out of the end of the first flexible elongate tubular member 16, the stent 126 will self expand toward its expanded condition until it is in engagement with the wall of the vessel in the vicinity of the occlusion forming the stenosis 76 to frictionally retain the stent in engagement with the vessel wall. As soon as the stent 126 is in engagement with the vessel wall, the second balloon 36 can be deflated as can the first balloon 19. The first deflated balloon 36 can then be withdrawn through the interior of the cylindrical stent 126. This can be followed by deflation of the first balloon 19 and the removal of the flexible elongate tubular member 16 with its first balloon 19 and the flexible tubular member 31 with its second balloon 36, along with the flexible elongate member 136 until the entire catheter assembly or apparatus 131 has been removed from the guiding catheter 63. Thereafter the guiding catheter 63 can be removed and the incision sutured as hereinbefore described.

In FIG. 11, there is shown another embodiment of an apparatus 151 incorporating the present invention which is particularly adapted for use treating a stenosis at or near a bifurcation appearing in an arterial vessel. The apparatus 151 is shown being used on a human being 152 showing the principal arteries and pulmonary veins of the human body. Thus there as shown, the abdominal aorta 153 branches into the common iliac 154 which branches into the external iliac 156 and the internal iliac 157. The external iliac branches into the deep femoral artery 158 and into the femoral artery 159. The abdominal aorta 153 extending in the opposite direction passes through the aortic arch 161 of the heart 162. The aortic arch 161 is connected to the common carotid 166 which extends into a bifurcation branching into the external carotid 167 the internal carotid 168. Similar bifurcations appear in the basilar artery which is an artery which is particularly inaccessible for surgical treatment.

As hereinafter explained, the apparatus 151 shown in FIGS. 11, 12 and 13 consists of a proximal occlusion balloon catheter 176 which can be considered to be a first catheter. The catheter 176 is formed of a flexible elongate tubular member 177 having proximal and distal extremities 178 and 179. The tubular member 177 is formed of a suitable material such as plastic and can have a suitable size ranging from 5 to 14 French and preferably 9 to 10 French. A balloon 181 is provided on the distal extremity 179 and is formed of a suitable elastic material. It is generally cylindrical in form and has its proximal and distal extremities secured to the tubular member 177 by suitable means such as an adhesive (not shown). The tubular member 177 is provided with a plurality of lumens therein. One lumen 182 serves as a balloon inflation lumen and extends from the proximal extremity 178. It can have a suitable size such as 0.024" and has port 183 in communication with the interior of the balloon 181. A manifold 186 formed of a suitable material such as plastic is mounted on the proximal extremity 178. A tubular member 187 is mounted in the manifold 186 and is in communication with the inflation lumen 182.

The tubular member 177 is also provided with a large lumen 191 having a suitable size as for example 0.045" which is adapted to slidably receive therein a therapeutic balloon catheter 192 and a perfusion balloon catheter 193. It is also provided with another lumen 196 having a suitable size as for example 0.026" which is adapted to receive a balloon-on-a-wire catheter 197. It is also provided with an aspiration lumen 201 having a suitable suize as for example 0.025" and an irrigation lumen 202 having a suitable size as for example 0.015". There is also provided another lumen 203 which can be used for other purposes.

The therapeutic balloon catheter 192 and the perfusion balloon catheter 193 are constructed in a manner similar to the balloon catheters hereinbefore described. Thus the perfusion balloon catheter 193 is provided with a flexible elongate tubular member 206 having proximal and distal extremities 207 and 208. A balloon 209 formed of an elastic material is secured to the distal extremity 208 by suitable means such as an adhesive (not shown) and is adapted to be inflated through a port 210 in communication with a balloon inflation lumen 211. The tubular member 206 is also provided with a blood perfusion lumen 212 which is centrally disposed therein. The proximal extremity 207 of the tubular member 206 is connected to a Y adapter or fitting 213 of which the central arm 214 is in communication with the blood perfusion lumen 212 and is provided with a Luer-type fitting 216. The side arm 217 of the fitting 213 is in communication with the balloon inflation lumen 211 and is provided with a Luer-type fitting 218 adapted to be connected to a source of pressure as hereinafter described.

The therapeutic balloon catheter 192 consists of a tubular member 221 having a proximal and distal extremities 222 and 223. A balloon 224 formed of a non-elastic material is secured to the distal extremity 223 by suitable means such as an adhesive. A port (not shown) is in communication with the interior of the balloon 224 and is in communication with a balloon inflation lumen 226. A Luer-type fitting 227 is mounted on the proximal extremity 222 and is in communication with the balloon inflation lumen 226. Another fitting 228 is mounted on the proximal extremity 222 and is in communication with a large centrally disposed lumen 229 which can receive the perfusion balloon catheter 193 for slidable movement as hereinafter described.

The balloon-on-a-wire catheter 197 is slidably mounted in the lumen 196 and consists of a guide wire 231 of a conventional construction having a suitable diameter as for example 0.018" and having a proximal and distal extremities 232 and 233. A balloon 234 formed of a non-elastic material is mounted on the distal extremity 233 and is secured thereto by suitable means such as an adhesive (not shown). The proximal extremity of the balloon 234 is secured to the distal extremity of a tubular member 236 formed of a suitable material such as plastic and which is coaxially disposed on the guide wire 231. The tubular member 236 extends the length of the guide wire to the proximal extremity and is connected to a Luer-type wye fitting 237 and is in communication with an annular lumen 238 disposed between the tubular member 236 and the exterior surface of the guide wire 231. The lumen 238 is in communication with the interior of the balloon 234 for inflating and deflating the balloon 234. The balloon-on-a-wire catheter 197 is adapted to be introduced through a fitting 241 carried by a tube 242 mounted in the manifold 186 and in communication with the lumen 196 in the multi-lumen elongate tubular member 177.

A tube 246 is mounted in the manifold 186 and is in communication with the large lumen 191 and is provided with a fitting 247 which is adapted to receive the perfusion balloon catheter 193 and the therapeutic balloon catheter 192 as hereinafter described. Another tube 251 is provided in the manifold 186 and is in communication with the aspiration lumen 201. It is provided with the fitting 252. Another tube fit 253 is mounted in the manifold 186 and is in communication with the irrigation lumen 202 and is provided with a fitting 254.

The various fittings for the catheter as hereinbefore described are adapted to be connected into a control console. The control console consists of a rectangular case 272 which is provided with a front panel 273.

A plurality of balloon inflation deflation devices 276 of a conventional type typically called endoflaters are mounted within the case 272 and have control handles 277 extending through vertically disposed slots 278 provided in the front panel. These endoflaters 276 are labeled as shown in FIG. 11 and are connected by tubing (not shown) through pressure gauges 281 mounted in the front panel 273 and are provided with needle indicators 282 to indicate the pressure being applied by the endoflater to the tubing. The tubing is connected in such a manner so that the endoflater 276 and the associated pressure gauge 281 are connected to a tube 286 which is provided with a mating fitting 287 adapted to mate with a fitting 188 so that it is in communication with the inflation lumen 182 of the proximal occlusion balloon catheter 176. In a similar manner, the tubing 288 is provided with a fitting 289 which mates with a fitting 218 of the balloon inflation lumen 211 of the perfusion balloon catheter 193 for inflating balloon 209. Similarly, tube 291 with its mating fitting 92 is adapted to mate with the fitting 237 for inflating the balloon 234. Similarly, the tube 293 with its fitting 294 mates with the fitting 227 in communication with the balloon inflation lumen 226 for inflating the balloon 224 of the therapeutic catheter 192. Another tube 296 which is provided with its fitting 297 mates with the fitting 252 that is in communication with the aspiration lumen 201. The tube 296 is in communication with the inlet of a blood pump 301 of a suitable type as for example a roller pump well known to those skilled in the art which is mounted within the case 272 and which is connected to a source of electrical power through electrical plug 302 connected into the case 272. The roller pump 301 is provided with an on/off switch 303 mounted on the front panel 273. After it passes through the pump 301, blood is supplied to a blood filter 306 of a conventional type and then is supplied through a tube 311 having a fitting 312 adapted to mate with the fitting 216 of the perfusion balloon catheter which is in communication with the perfusion lumen 212.

A three-way valve 316 is associated with each of the endoflaters 276 and has a control knob 317 extending through the front panel 273 and is adaptable to be moved between three positions with a center off position and an aspiration position in a counter-clockwise direction and a pressurized position in a clockwise position as viewed in FIG. 14.

Operation and use of the apparatus 151 may now be briefly described as follows. Let it be assumed that it is desired to treat a stenosis occurring in a bifurcation in a carotid artery as depicted by the illustrations shown in FIGS. 15A through 15D. As shown in the illustration in FIG. 15A, let it be assumed that a stenosis is present adjacent the bifurcation 167 and in the internal carotid 169 and that it is desired to treat this stenosis in accordance with the apparatus 151 of the present invention in performing the method of the present invention. The proximal occlusion balloon catheter 176 is loaded with the therapeutic balloon catheter 192 slidably mounted over the perfusion balloon cathete 193 and both are slidably mounted in the main lumen 191. The balloon-on-a-wire catheter 197 is slidably mounted in the lumen. While the patient is being prepared for the procedure, all of the lumens in the catheters of the apparatus are flushed with saline to remove all air from the lumens. They are then connected to the control console 271 in the manner hereinbefore described and as shown in FIG. 11. An incision 326 (see FIG. 11) is made in the femoral artery in the left leg of the patient and a guiding catheter (not shown) similar to the type utilized in angioplasty is introduced through the femoral artery 159. This guiding catheter is advanced until it is near the aorta arch 161. Thereafter, the first or proximal occlusion balloon catheter 176 has its distal extremity 179 introduced into the guiding catheter and advanced in the guiding catheter. It is advanced so that its distal extremity 179 enters the common carotid and is near the bifurcation 167. The balloon 181 is inflated by operating the control handle 277 associated with the proximal occlusion balloon 181 as shown in FIG. 15A to create the desired pressure within and to inflate the elastic balloon 181 so that it occludes the common carotid just proximal of the stenosis 324. As soon as this occurs, the roller pump 301 is turned on by operating the on/off switch 303 to create a negative pressure on the distal side of the balloon 181 to cause blood to flow in a reverse direction as shown by arrows 326 to thereby change the directional flow of blood from the internal and external carotids away from the brain rather than to the brain. The blood travels into the aspiration lumen 201 as indicated by the arrows 326 and into the tube 251 through fittings 252 and 297 and tube 296 to the roller pump 303. The blood after passing through the roller pump 303 passes through a blood filter 306 and then passes into the tube 311 and the fitting 312 and connected to the fitting 289 of the perfusion catheter 193. Alternatively, the fitting 312 can be connected to another fitting 331 mounted on a tube 332 introduced into the venous side of the circulatory system of the patient's body, as for example into the vein in the right leg of the patient 152 as shown in FIG. 11. Any debris or emboli in the aspirated blood being pumped will be filtered out by the blood filter 306.

As soon as or during the time this retrograde circulation of blood is established through the roller pump 301, the perfusion balloon catheter 193 extending proximally from the fitting 247 is advanced into the internal carotid 169 past the stenosis 321 at the bifurcation 167. If necessary, a guide wire can be utilized which can be introduced through the perfusion lumen 212 to aide in advancing the perfusion balloon catheter 193 into the internal carotid 169. Any emboli or debris dislodged from the stenosis 321 by crossing the same either by the guide wire or by the distal extremity of the catheter 193 will be picked up by the retrograde flow of blood which is being aspirated through the proximal occlusion balloon catheter 176 to thereby prevent any emboli or debris from entering the brain of the patient. The elastic perfusion balloon 209 is then inflated as shown in FIG. 15B using the appropriate endoflater to inflate the balloon to the desired pressure while watching the associated pressure gauge. As soon as occlusion occurs, perfusion of blood can be started as hereinafter described.

Prior to or after the balloon 209 of perfusion catheter 193 has been inflated, the balloon-on-a-wire catheter 197 extending proximally of the fitting 241 is advanced into the external carotid 169 as shown in FIG. 15C. The balloon 234 is then expanded by use of the appropriate endoflater to supply an inflating medium through the fitting 237 to occlude the external carotid 169. As soon as occlusion has been accomplished in both the external and internal carotids, retrograde flow of blood is terminated by shutting off the roller pump 301. It should be appreciated that if desired, automatic controls can be provided whereby when a certain pressure is reached in each of the balloons 209 and 234 the roller pump would automatically be shut off to stop retrograde flow. By this procedure, it can be seen that the lesion of stenosis 321 has been bracketed by the balloons 181, 209 and 234. Prior to that occurring, retrograde flow of blood is established to prevent any emboli or debris from moving towards the brain.

As soon as retrograde flow of blood has been terminated, perfusion of blood is started. This can be accomplished by connecting a cannula (not shown) to the fitting 216 of the perfusion catheter 206 and to obtain a supply of blood from the femoral artery in the other leg of the patient. Alternatively, an outside blood supply can be used. Thus fresh blood will be supplied from the femoral artery of the patient directly into the perfusion balloon so that it is discharged distally of the perfusion balloon 209 as shown by the arrows 327 to continue to supply blood to the carotid artery. It has been found that it is unnecessary to a supply perfusion of blood to the external carotid artery because there is sufficient auxiliary circulation in that carotid artery during the time the procedure is taking place.

In the event there is inadequate pressure on the arterial blood being profused to overcome the resistance in the lumen 169, the roller pump 301 can be utilized by merely operating the same in a reverse direction and connecting it between the cannula and the perfusion catheter.

After the lesion or stenosis 321 has been bracketed as hereinbefore described and a working space 336 formed adjacent the stenosis or lesion 321, a therapeutic procedure can be employed. By way of example this can consist of advancing the therapeutic balloon catheter 192 over and axially of the perfusion catheter 193 to bring its balloon 224 into registration with the stenosis 321 as shown in FIG. 15D. Thereafter, the balloon 224 can be inflated by use of the appropriate endoflater as hereinbefore described to cause the inelastic balloon to be pressurized to a pressure of 10 to 15 atmospheres to compress the stenosis 321. Prior to or during this procedure it may be desirable to introduce a saline or heparin solution or a radiopaque contrast liquid into the working space 336. This can be accomplished by introducing this liquid through the injection lumen 202. If desired, this can be accomplished prior to terminating the aspiration procedure hereinbefore described. Also it should be appreciated that if desired a small endoscope can be inserted through one of the lumens to view the area within the working space. Alternatively, if desired an ultrasonic probe can be utilized to view the area in which the lesion is disposed.

As hereinbefore described with a previous embodiment, in place of the therapeutic balloon catheter, other types of catheters can be utilized as for example one incorporating an atherectomy device of the type hereinbefore described to facilitate removal of the stenosis. It is readily apparent that during these procedures if it is necessary to supply a saline solution or a heparinized solution into the working space that the working space can also be continued to be aspirated to remove any debris or emboli which occur during the procedure.

Let it be assumed that the desired therapeutic actions have been undertaken and that the stenosis 321 has been reduced and substantially eliminated so that there is adequate flow through the internal carotid. If it can be seen that there also is a stenosis in the external carotid, the balloon-on-a-wire catheter 197 and the perfusion catheter 193 can be withdrawn and moved so that they enter the opposite carotid to permit therapeutic treatment of a stenosis occurring in the other carotid.

When all the desired therapeutic procedures have been accomplished, the supply of saline or contrast solution can be terminated and the therapeutic balloon 224 deflated. The balloon 234 of the balloon-on-a-wire catheter can be deflated as well as the perfusion balloon 209. Perfusion of blood through the perfusion catheter can be terminated. The perfusion balloon catheter 193 and the balloon-on-a-wire catheter 197 can be retracted into the main multi-lumen tubular member 177 of the proximal occlusion balloon catheter after which-the perfusion balloon catheter can be withdrawn carrying with it the other catheters disposed therein. Thereafter, the guiding catheter can be removed and a suture applied to the incision made to gain access to the femoral artery.

It is readily apparent that similar procedures can be carried out with respect to other vessels in the body, such as saphenous vein grafts in the heart, and particularly with respect to vessels in the brain where it is difficult if not impossible to employ surgical procedures as for example with respect to the basilar arteries in which bifurcations appear.

As also herein before explained, the catheter apparatus of the present invention can be utilized for deploying stents. Where that is desirable the apparatus of the present invention, perfusion can be accomplished during employment of the stent.

From the foregoing it can be seen that an apparatus and method has been provided for treating occluded vessels and particularly for treating carotid arteries. The apparatus and method of the present invention is particularly advantageous for the carotid arteries because it permits access to portions of the carotid arteries which are not accessible by surgery. The catheter apparatus assembly and method of the present invention is also particularly useful for treating other occluded vessels but particularly the carotid arteries because it makes possible the removal of plaque without endangering the patient. An operating or working space is provided while shunting blood around the working space so that there is continued blood flow in the vessel to support the functions which are normally supported by the vessel. As also pointed out above, the apparatus and method of the present invention are particularly useful in connection with vessels having bifurcations therein and in which the stenosis occurs at or near the bifurcation. From the foregoing it can be seen with the apparatus and method of the present invention, retrograde flow of blood is accomplished during deployment of the device to prevent undesired travel of emboli. Occlusion of the vessels is provided to obtain a working space by bracketing the working space with balloons while at the same time maintaining perfusion of blood making it possible to utilize a substantial period of time for undertaking therapeutic procedures with respect to the bracketed stenosis.

What is claimed is:

1. A method for treating occluded vessels comprising:
   first advancing a first catheter having a first inflatable balloon mounted thereon into a blood vessel until the first balloon is positioned proximal to a stenosis in the blood vessel;
   inflating the first balloon to occlude the blood vessel; and then
   advancing a second catheter across said stenosis until the second catheter is positioned distal to said stenosis.

2. The method of claim 1, wherein said blood vessel is a saphenous vein graft.

3. The method of claim 1, wherein said blood vessel is a carotid artery.

4. The method of claim 1, wherein said second catheter has an inflatable balloon mounted thereon, and wherein the method further comprises inflating the balloon on the second catheter after said second catheter is positioned distal to said stenosis.

5. A method for treating occluded vessel comprising:
   first inhibiting a flow of blood across a stenosis in a blood vessel in a proximal to distal direction; and then
   advancing a catheter across said stenosis in a proximal to distal direction.

6. The method of claim 5, wherein said vessel is substantially occluded at a site proximal to said stenosis to inhibit said flow of blood.

7. The method of claim 6, wherein said substantial occlusion is provided by inflating an inflatable balloon within said blood vessel at a site proximal to said stenosis.

8. The method of claim 5, wherein the blood flow is inhibited prior to advancing the catheter across the stenosis.

9. The method of claim 5, wherein the blood flow is inhibited while the catheter is advanced across the stenosis.

10. The method of claim 5, wherein said catheter is a guidewire.

11. The method of claim 5, wherein said catheter is a hollow guidewire bearing an occlusive device.

12. The method of claim 5, wherein the blood flow is inhibited across the stenosis by negative pressure near said stenosis.

13. A method for treating a stenosis in a bifurcated blood vessel comprising:
   first advancing a first catheter having a first occlusive device mounted thereon into said blood vessel until the first occlusive device is positioned proximal to the stenosis;
   activating the first occlusive device to occlude the blood vessel;
   advancing a second catheter having a second occlusive device mounted thereon across said stenosis until the second occlusive device is positioned distal to said stenosis and in a first branch of the vessel;
   activating the second occlusive device on the second catheter;
   advancing a third catheter having a third occlusive device mounted thereon until the third occlusive device is positioned in a second branch of the vessel; and
   activating the third occlusive device on the third catheter.

14. The method of claim 13, wherein said bifurcated blood vessel is a carotid artery.

15. The method of claim 13, wherein said occlusive devices are inflatable balloons and wherein the activating of the occlusive devices comprises inflating the balloons.

16. The method of claim 5, wherein said blood vessel is a carotid artery.

17. The method of claim 5, wherein said inhibiting the flow of blood is achieved by delivering a first catheter having an occlusive device mounted thereon into the blood vessel and activating the occlusive device.

18. The method of claim 17, further comprising advancing a second catheter having a second occlusive device mounted thereon across said stenosis in a proximal to distal direction after delivery and activation of the first occlusive device.

19. The method of claim 18, further comprising activating the second occlusive device after the second catheter is advanced across the stenosis.

20. The method of claim 19, wherein the first and second occlusive devices are inflated balloons, and the activation comprises inflating the balloons.

* * * * *